US006972415B2

United States Patent
Schaible et al.

(10) Patent No.: US 6,972,415 B2
(45) Date of Patent: Dec. 6, 2005

(54) FLUID TREATMENT SYSTEM WITH UV SENSOR AND INTELLIGENT DRIVER

(75) Inventors: Uwe D. Schaible, Ancaster (CA); Steven M. Leatherland, Hamilton (CA); William T. Mennen, Guelph (CA); Robert J. Cazzola, Guelph (CA)

(73) Assignee: R-Can Environmental Inc., Guelph (CA)

( * ) Notice: Subject to any disclaimer, the term of this patent is extended or adjusted under 35 U.S.C. 154(b) by 4 days.

(21) Appl. No.: 10/670,272

(22) Filed: Sep. 26, 2003

(65) Prior Publication Data

US 2004/0061069 A1    Apr. 1, 2004

Related U.S. Application Data

(60) Provisional application No. 60/413,554, filed on Sep. 26, 2002.

(51) Int. Cl.[7] .......................... B01D 19/00; C02F 1/20; C02F 1/32
(52) U.S. Cl. ...................... 250/436; 250/437; 250/438; 250/432 R; 250/504 R; 250/492.1; 210/748
(58) Field of Search ................................ 250/436–438, 250/432 R, 504 R, 492.1, 493.1, 494.1; 210/87–90, 210/85, 739, 742, 748; 422/24, 186, 186.3

(56) References Cited

U.S. PATENT DOCUMENTS

| 4,471,225 | A |   | 9/1984  | Hillman |   |
|-----------|---|---|---------|---------|---|
| 4,849,115 | A |   | 7/1989  | Cole et al. |   |
| 4,876,014 | A | * | 10/1989 | Malson ........................ | 210/668 |
| 4,959,142 | A |   | 9/1990  | Dempo |   |
| 5,019,256 | A |   | 5/1991  | Ifill et al. |   |
| 5,144,146 | A | * | 9/1992  | Wekhof ................... | 250/492.1 |
| 5,151,252 | A | * | 9/1992  | Mass ....................... | 422/186.3 |
| 5,230,792 | A | * | 7/1993  | Sauska et al. ................ | 210/97 |
| RE34,513  | E |   | 1/1994  | Ellner |   |
| 5,332,388 | A |   | 7/1994  | Schuerch et al. |   |
| 5,368,826 | A |   | 11/1994 | Weltz et al. |   |
| 5,372,781 | A | * | 12/1994 | Hallett et al. ............ | 422/186.3 |
| 5,471,063 | A |   | 11/1995 | Hayes et al. |   |
| 5,487,088 | A |   | 1/1996  | Weltz et al. |   |
| 5,505,912 | A | * | 4/1996  | Hallett .................... | 422/186.3 |
| 5,698,091 | A | * | 12/1997 | Kuennen et al. ............. | 210/87 |
| 5,846,437 | A |   | 12/1998 | Whitby et al. |   |
| 5,952,663 | A |   | 9/1999  | Blatchley, III et al. |   |
| 6,117,335 | A | * | 9/2000  | Bender ...................... | 210/745 |
| 6,143,183 | A |   | 11/2000 | Wardwell et al. |   |

(Continued)

*Primary Examiner*—John R. Lee
*Assistant Examiner*—Bernard E. Souw
(74) *Attorney, Agent, or Firm*—Anne Kinsman; Borden Ladner Gervais LLP (57) ABSTRACT

A fluid treatment system in which the fluid to be treated is irradiated with ultraviolet light (UV). The system includes a sensor with capabilities for detecting multiple fluid treatment parameters, such as UV intensity level and fluid flow. The sensor contains a combination of a UV sensing means such as a photodiode, a flow sensing means such as a vibration sensitive microphone, and associated electronics for processing and transmitting data pertaining to the fluid treatment parameters. The system can also include or alternatively include an intelligent driver that powers a UV lamp and has the novel capabilities to receive, process, respond to, and display multiple fluid treatment parameter signals from one or more sensors without the need for additional signal processing and/or control devices. Specifically, in a preferred embodiment, the power being delivered to the UV lamp will be adjusted as warranted by the intelligent driver's analysis of at least one fluid treatment parameter, such as flow condition.

27 Claims, 6 Drawing Sheets

U.S. PATENT DOCUMENTS

| | | |
|---|---|---|
| 6,193,939 B1 | 2/2001 | Kozlowski |
| 6,200,466 B1 * | 3/2001 | Bender ............... 210/96.1 |
| 6,264,836 B1 * | 7/2001 | Lantis ............... 210/188 |
| 6,313,468 B1 | 11/2001 | Wedekamp |
| 6,316,877 B1 | 11/2001 | Kaas |
| 6,317,051 B1 * | 11/2001 | Cohen ............... 340/603 |
| 6,436,299 B1 * | 8/2002 | Baarman et al. ............ 210/748 |
| 6,451,202 B1 * | 9/2002 | Kuennen et al. ............ 210/136 |
| 6,586,172 B1 * | 7/2003 | Gunn et al. ............... 435/2 |
| 6,707,048 B2 * | 3/2004 | Hallett et al. ............... 250/431 |
| 2002/0033369 A1 * | 3/2002 | Bender ............... 210/748 |
| 2003/0071224 A1 * | 4/2003 | Hallett et al. ............ 250/432 R |
| 2003/0213755 A1 * | 11/2003 | Hanbli ............... 210/748 |
| 2004/0020862 A1 * | 2/2004 | Baca et al. ............... 210/748 |
| 2004/0061069 A1 * | 4/2004 | Schalble et al. ........ 250/432 R |

* cited by examiner

FLUID TREATMENT SYSTEM WITH UV SENSOR AND INTELLIGENT DRIVER

CROSS-REFERENCE TO RELATED APPLICATIONS

This application claims the benefit of priority from U.S. Provisional Application No. 60/413,554, filed Sep. 26, 2002, the entire contents of which are incorporated herein by reference.

FIELD OF THE INVENTION

The present invention generally relates to fluid treatment systems that utilize ultraviolet light (UV), typically requiring an electrical ballast or driver to operate a UV emitter, a defined fluid treatment zone, and can include means to detect the level of UV within the fluid treatment zone.

BACKGROUND OF THE INVENTION

Existing products commonly found in the market-place include air and water treatment devices utilizing ultraviolet light as a means to inactivate, convert, or destroy some portion of undesirable contaminant that may be present in the fluid, which can be gas or liquid. For example, treatment devices using UV to inactivate pathogenic micro-organisms in water are commonplace and well established in the art. Such devices range in capacity from less than 0.5 US gallons per minute to several thousand gallons per minute. In practice, the number of users can range from one, as in the case of a small dwelling, to several million as in the case of large municipal water systems: hence the large range in flow capacity.

The use of UV as a means to inactivate micro-organisms in water has been shown to be effective and advantageous over chemical disinfection systems as the UV does not require handling of dangerous chemicals and does not lead to the formation of undesirable disinfection by-products. Further, the use of small disinfection units at the point of water entry into a building (POE), or even at the point of use (POU), such as the faucet, has been shown to be advantageous even if the municipal water supply is centrally disinfected, as there have been several documented cases in which the centralized municipal disinfection system has malfunctioned or the municipal distribution system has become contaminated.

The level of pathogen inactivation and flow rate of treated fluid that can be delivered is, in a simplistic description, highly dependent on the product of the UV intensity within the treatment zone and the duration of time that the water is exposed to the UV within the treatment zone. Therefore, it can be seen that for optimum treatment performance it is necessary for the system to acquire and respond to information regarding the light intensity and flow condition within the reactor. Such information is typically acquired and transmitted by parameter specific sensors, i.e. one sensor for each parameter. Currently available systems where multiple fluid treatment parameters are monitored require a separate control and one or more display devices to receive, process, respond to, and display multiple sensor signals.

The main problem, particularly with the smaller UV treatment systems, is that although they may include a sensor to detect the UV level, they do not incorporate any means to detect water flow, forcing these systems to operate under assumed conditions of continuous maximum flow-rate. Such an assumption causes the ultraviolet emitter to be operated continuously at its maximum power, even if there is little or no water flow. In practice it is common for these smaller UV treatment systems, as might be found in a household, to experience no-flow or low-flow conditions for a large percentage of time. Hence, the inability to detect flow conditions leads to undesirable heating of the water, unnecessary electricity usage, reduction of the emitter's UV output, and possible shortening of the UV emitter's life due to overheating.

To further exacerbate the above problem, traditional water flow sensors are either too costly, as in the case of magnetic flux flow sensors, for the purchasers of small systems or are unreliable, as in the case of paddlewheel flow-meters which can become stuck and hence fail to indicate flow altogether.

Another problem with conventional products is that even if an external flow sensor is incorporated, the additional devices required to receive, process, respond to, and display this signal are prohibitively expensive and technically complicated for the purchasers of small systems.

Further, conventional drivers for powering the UV emitters, do not have the capability to display detailed information pertaining to the fluid treatment parameters and diagnostic information pertaining to the system operation. Typically, the information is limited to what can be displayed by indicator lights.

In all UV treatment systems, the UV transmittance (UVT) of the fluid, or the transparency of the fluid to UV light, is an important parameter that is typically monitored by a dedicated device or assumed to be at no less than some particular value. Unfortunately, dedicated UVT monitoring devices are costly and require connection to an additional controller if the system is to respond to the varying UVT. In many applications, these devices are not included due to their cost and complexity. In some applications that do not utilize a UVT monitoring device, the assumed UVT value may be lower than actual, resulting in the system using more energy than required. Conversely, if the assumed UVT value is higher than actual, the system may deliver inadequate UV dose.

It is, therefore, desirable to provide an improved UV treatment system which is capable of monitoring, displaying, and responding to fluid treatment parameters and diagnostic information without undue cost and complexity.

SUMMARY OF THE INVENTION

It is an object of the present invention to obviate or mitigate at least one disadvantage of previous UV fluid treatment systems. Generally, the present invention provides a fluid treatment system with a UV sensor and intelligent driver/controller.

More specifically, the present invention relates to a UV sensor with novel fluid flow detection capabilities that provides signals for multiple fluid-treatment parameters, for example UV intensity and fluid flow. Further, an intelligent ballast, or driver, or controller, as part of the fluid treatment system, has the novel capability for receiving, processing, responding to, and displaying of one or more parameters based on one or more input signals.

The fluid treatment system of the present invention includes one or more sensors, each uniquely addressed, connected to and communicating directly with at least one intelligent driver for powering one or more UV emitters. The system allows processing of and responses to signals from one or more sensors, which can monitor one or more operating parameters, without the need for external processing devices. It should be noted that the present invention is not limited to the use of sensors described herein: for example, one or more temperature sensors can be connected provided that they are compatible with the communication bus. Further, the system can also comprise more than one intelligent driver, or other device, that is suitably compatible with the communication bus. An interlock switch, to be connected to the appropriate microprocessor input, can be included in the system to indicate to the microprocessor that the UV emitter should be disabled according to the state of the switch (open or closed).

According to an aspect of the present invention, a UV fluid treatment system comprises: an ultraviolet light source; a system sensor, the system sensor having an ultraviolet light sensing means and a sound/vibration sensing means (for example, an acoustic sensor) for detection of fluid flow; light source control means for controlling the ultraviolet source in response to fluid flow detected by the sensor; and a sound/vibration generation means for allowing self-diagnosis of the sound/vibration sensing means. The light source control means can be connected to one or more sensors for receiving input signals from the one or more sensors and the light source control means includes processing means for processing the received signals and a display for displaying information relating to operational parameters of the system.

According to another aspect of the present invention, there is provided a single sensor device that provides multiple signals pertaining to multiple fluid treatment parameters, specifically in the preferred embodiment the parameters of UV level and fluid flow condition.

According to still another aspect of the present invention there is provided a reliable fluid-flow sensor integrated into a UV sensor at cost significantly lower than that of traditional fluid flow sensors.

According to yet another aspect of the present invention there is provided a fluid-flow sensor with self-diagnostic capabilities and inherent "fail-safe" characteristic.

According to a further aspect of the present invention there is provided a single device for sensing multiple fluid treatment parameters that is no more complex to incorporate into a fluid treatment system than a single sensor.

According to still further aspect of the present invention there is provided an intelligent driver for powering the UV emitter that is capable of receiving, processing, and responding to multiple fluid treatment parameter signals from one or more sensors without the need for additional signal processing and/or control devices. Specifically, in a preferred embodiment, the intelligent driver will be able to reduce the power being delivered to the UV emitter if warranted by the microprocessor's analysis of the fluid treatment parameters, such as, for example, flow condition.

According to a still further aspect of the present invention there is provided an intelligent driver that is capable of analyzing multiple UV level signals, for example from different locations within the treatment zone, to determine parameters such as UVT of the fluid and/or fouling of the UV emitter and/or condition of the UV emitter. The fluid UVT can be calculated by the microprocessor from two UV levels within the fluid, provided that each level is monitored at a different distance from the UV emitter. Additional information, such as the age of the UV emitter or the UV level coming directly from the UV emitter, can be utilized by the microprocessor to determine whether or not the UV emitter is becoming fouled.

According to a still further aspect of the present invention there is provided an intelligent driver for powering the UV emitter that is capable of displaying graphical and/or text information pertaining to one or more fluid treatment parameters and/or system operation parameters without the need for external processing or display devices.

According to a still further aspect of the present invention there is provided an intelligent driver for powering the UV emitter that is capable of monitoring and diagnosing system operation, and displaying the relevant graphical and/or text information without the need for external monitoring, diagnostic, or display devices.

According to a still further aspect of the present invention there is provided a fluid treatment system capable of irradiating a fluid with UV and monitoring, responding to, and displaying multiple treatment parameters, for example UV and flow and system operation/diagnostic information, said system requiring no devices other than the following: at least one UV emitter; at least one intelligent driver; at least one sensor; and at least one treatment zone for irradiating fluid.

According to a still further aspect of the present invention there is provided a fluid treatment system that is capable of utilizing a safety interlock switch to disable a UV emitter depending on the switch's state (open/closed), without the need for additional control devices or power relays other than those included within the driver.

According to a still further aspect of the present invention there is provided an intelligent driver, for powering the UV emitter that has the capability to be reprogrammed from an external device. Examples of this improved functionality would be to change the language of the display text or change alarm threshold levels or change microprocessor algorithms.

The UV sensor of the present invention includes, within a single sensor housing, a UV light sensing means and a sound/vibration sensing means for detecting fluid flow. Additional features of the present invention contained within the single sensor housing include: a sound/vibration generation means that allows for self-diagnosis of the sound/vibration sensing means; a microprocessor; and a communication bus. A device address select capability can be incorporated, allowing each single sensor to be identified by a unique address.

The UV sensing means can comprise a window which transmits light from the fluid treatment chamber to a light detector such as a photodiode. The sound/vibration sensing means comprises a microphone and its associated signal amplification and processing electronics. The sound/vibration generation means can comprise an acoustical sounder, or buzzer, and its associated drive electronics. A microprocessor, such as a readily available 8-bit microcontroller, is adequate to read, process and store the various sensor signals. A device address select can be composed of an array of switches interfaced to logic level input pins of the microprocessor. The communication bus can comprise a 2 wire $I^2C$ bus serial interface.

Preferably, any associated signal amplification and processing electronics are also enclosed in the sensor housing. The signals processed by the sensor can be transmitted via a single communication line. The number and type of parameters monitored by a single sensor are not limited to those previously described: for example, a single sensor can include means to sense temperature and/or multiple UV sensing means to detect the UV level at a different locations within the treatment zone. The temperature sensor signal can be alternatively used to provide an indication of the fluid flow condition: for example, if the UV emitter is ON the fluid temperature will rise in the case of a no-flow condition.

The intelligent driver includes the following within a single housing: a communication bus such that it can connect with and distinguish between one or more external devices, such as one or more sensors and/or other intelligent drivers; and a microprocessor for processing, analyzing, and responding to one or more signal inputs. A variable power drive circuit can be included such that the power delivered to the UV emitter is adjusted by the microprocessor in accordance to the analysis of one or more sensor input signals. A further feature is the inclusion of a display capable of showing graphic or text information regarding the operational parameters of the driver and/or other system components. A switch for changing the display screen or operational settings can be incorporated directly within the display. For example the display/switch can be the NKK Smart Switch # IS15ANCP4CF, which combines a pushbutton with programmable 36×24 pixel graphic LCD display. The microprocessor and display contained within the driver allow advantageous monitoring and reporting of system operational parameters such as: UV level; fluid flow condition; remaining lamp life; expended lamp life; and total system operating time.

Another feature of the intelligent driver is that it can be reprogrammed from an external programming device, simply by connecting the external device to the communication bus an initiating the driver's "reprogram" mode. In the preferred embodiment, the driver's reprogram mode is initiated at power-up if the external programming device is connected to the communication bus.

Yet another feature of the intelligent driver is the inclusion of a safety-interlock input to the microprocessor, which allows the microprocessor to disable the operation of the UV emitter under certain conditions. For example, this input can be connected to an external switch that would change state (open/closed) depending on whether or not the UV emitter is fully installed into a treatment chamber: in this example, the microprocessor would prevent the UV emitter from being energized if it were not fully installed in the treatment chamber.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Generally, the present invention provides a fluid treatment system with UV sensor and intelligent driver/controller. More specifically, the present invention relates to a UV sensor with novel fluid flow detection capabilities that provides signals for multiple fluid-treatment parameters, for example UV intensity and fluid flow. Further, an intelligent ballast, or driver, or controller, as part of the fluid treatment system, has the novel capability of receiving, processing, responding to, and displaying of one or more parameters based on one or more input signals. The UV fluid treatment system is preferably for small enterprise and consumer use. The system includes a fluid treatment zone having a fluid inlet and a fluid outlet. A UV emitter and a sensor unit are disposed within the fluid treatment zone. The sensor unit includes multiple sensing means, such as fluid flow sensing means to sense fluid flow within the fluid treatment zone and UV sensing means to sense UV light levels. An intelligent driver receives signals muliple sensing means and controls operation of the UV emitter in response to the signals received. An indicator, such as a display, is in communication with the intelligent driver and provides a user with information related to operation of the fluid treatment system. The present invention also provides a sensor unit, or sensor means, for such a fluid treatment system, and an intelligent driver.

Figure 1:
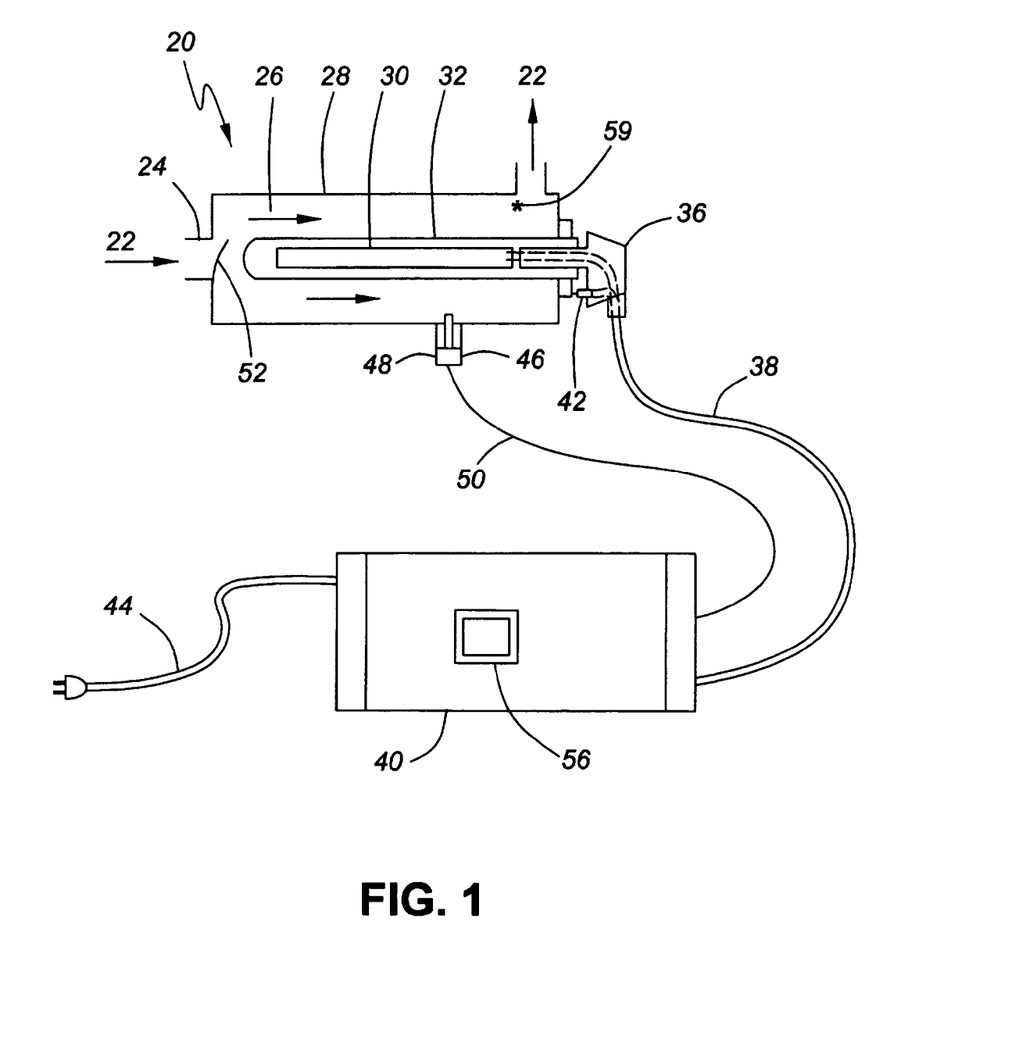
FIG. 1 is a fluid treatment system according to an embodiment of the present invention.

FIG. 1 is an example embodiment of the present invention. FIG. 1 illustrates a fluid treatment system 20 in which the fluid to be treated 22 enters through an inlet 24 to a treatment zone 26. The treatment zone is defined as the region within chamber wall or walls 28 through which the fluid flows and is irradiated by light from one or more UV emitters 30. The one or more UV emitters 30 of the illustrated system are mercury vapour lamps, but other UV emitting devices known in the art can be used. In this particular example, the one or more UV emitters 30 are contained within one or more UV-transparent housings 32 typically made from fused silica (commonly referred to as "quartz") to prevent the fluid 22 from directly contacting the UV emitter 30. Other UV-transparent materials are available, such as Teflon. Also in this illustration a separate fluid exit 34 is provided to allow continuous flow through the treatment zone 26. Note that various sealing means, such as compressible O-rings, to keep the fluid appropriately contained are well known in the art and are omitted in these descriptions.

The UV emitter 30 is electrically connected via plug 36 and cable 38 to intelligent driver 40, such that the UV emitter 30 can be powered by the driver 40. A proximity switch 42 is incorporated into plug 36 such that switch contacts are in one state (open or closed) if the plug 36 is fully seated in the operating position, and the contacts are in the opposite state if the plug is not fully seated in the operating position. Cable 38 also contains electric conductors that connect switch 42 to driver 40. In order for the system to operate, the driver 40 requires electric power to be connected from an external source via cord 44.

In this example, a sensor 46 is comprised of a single sensor housing which attaches to a port 48 in chamber wall 28. The housing includes a sealed UV-transparent window that keeps fluid 22 from escaping the treatment zone 26 while still allowing UV light to pass into sensor 46 and fall incident upon a conventional UV sensing means contained within the housing. Also within the single sensor 46 housing of this particular embodiment is a sound/vibration sensing means for detecting fluid flow. The sensor 46 transmits data corresponding to both the UV and flow parameters along a communication cable 50 to intelligent driver 40. Cable 50 also provides electrical power and command signals from intelligent driver 40 to sensor 46.

Note that the communication of data and commands between sensor 46 and driver 40 could, as an alternative to cable 50, be achieved via wireless communication (e.g. radio frequency, infrared, etc.) techniques commonly known. If cable 50 were eliminated, an alternative power source for the sensor 46 would be required, such as a battery contained within housing, or a photocell array being struck by light from the within the fluid treatment zone, or a photocell array being struck by light from outside of the fluid treatment zone.

When fluid 22 is passed through the fluid treatment zone 26, sound/vibrations will be created which are then detected by a sound/vibration sensing means within sensor 46. Once the detected sound/vibration level is above some predetermined threshold, an electric signal indicating the presence of flow can be communicated to and monitored by other connected devices of the treatment system, in this case intelligent driver 40. The driver 40 can then respond to this information: for example, it can adjust power to the UV emitter 30 if the flow condition warrants, thereby conserving energy, reducing undesirable heating of the fluid 22, and preventing overheating of the UV emitter 30 and related detrimental effects on emitter life and efficiency.

Also shown in FIG. 1 are a sound generation reed 52 and a sound generating paddlewheel 54 which can be included along the fluid flow path, though not necessarily inside the treatment zone 26. Such sound generating devices generate sound/vibrations dependent on flow condition, and, though optional, may be desirable to provide more specific sound signals for detection by the sensing means contained within sensor 46. For example, the paddlewheel 54 can generate a sound with frequency that is proportional to the fluid flow-rate, allowing the driver 40 to process and respond to a continuum flow signal rather than just a two-state signal.

When the UV emitter 30 is powered ON, light strikes the UV sensing means contained within sensor 46 to generate an electric signal which can be communicated to and monitored by other connected devices of the treatment system, in this case intelligent driver 40. The driver 40 can then respond to this information: for example, if the UV level is inadequate an alarm can be generated and/or power to the UV emitter can 30 be increased. The intelligent driver 40 of this particular embodiment also contains a display 56.

Figure 2:
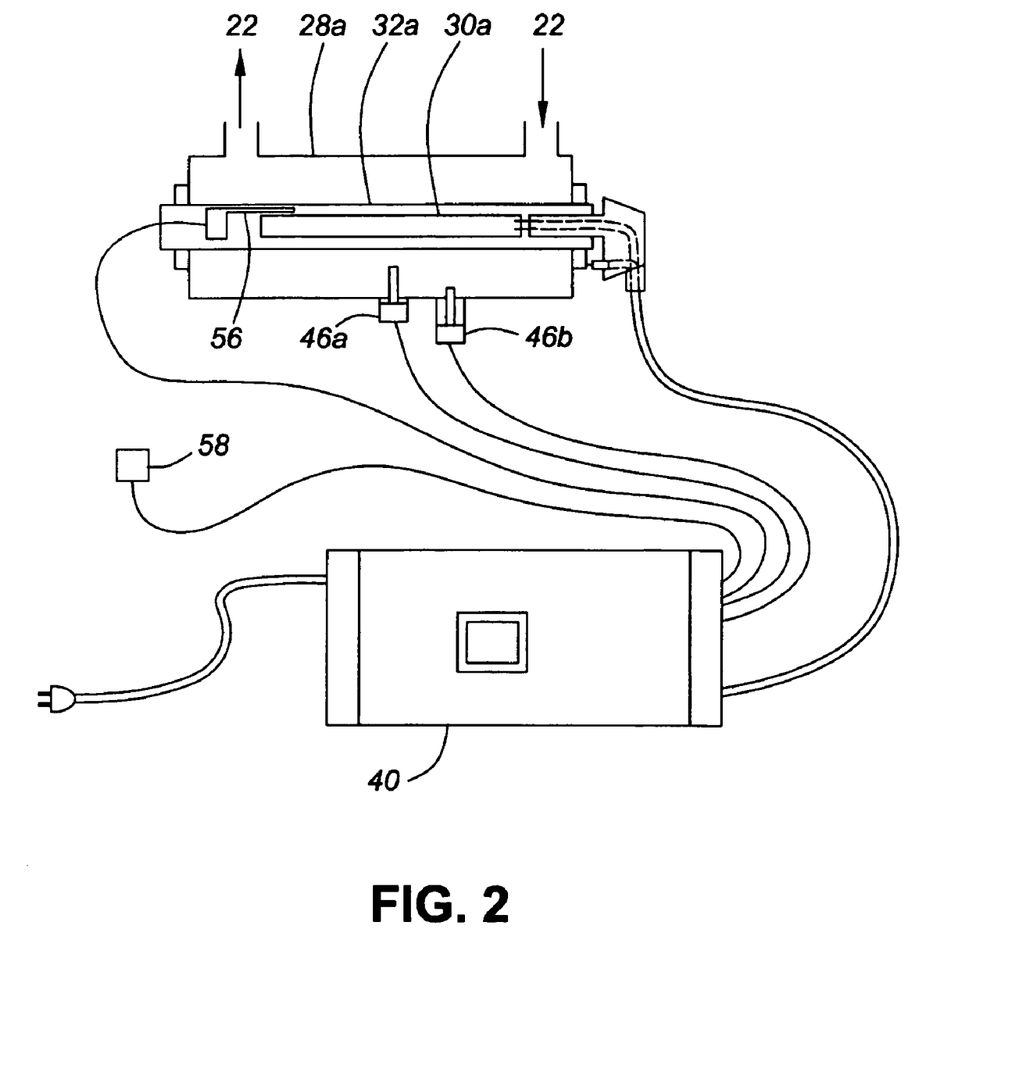
FIG. 2 is a fluid treatment system according to another embodiment of the present invention.

FIG. 2 illustrates another system example embodiment, in which multiple identical sensors 46a, 46b are installed to chamber wall 28a and connected to the same intelligent driver 40. This multiple sensor 46 connection is possible via the address select contained within the sensors 46a, 46b and the capability of the driver 40 to distinguish between the unique addresses. Note that one of the sensors 46a is positioned such that it is closer to the UV transparent housing 32a. In this manner, the UV light from emitter 30a must travel farther to reach the UV sensing means of sensor 46b than that of sensor 46a. Since the portion of UV absorbed by the fluid 22 is highly dependent of both the UVT of the fluid and the distance through which the UV light has travelled through the fluid, it is possible to determine the UVT of the fluid. Of course, those skilled in the art will recognize that the algorithm for calculating UVT must also take into account the independent geometric dispersion of the UV light as it travels farther from the UV emitter. The intelligent driver 40 can perform the calculations, display the results, and respond appropriately in the form of alarms and/or adjustment of power delivered to the UV emitter 30a.

As shown in FIG. 2, multiple sensors can be connected to the intelligent driver 40 provided that they use a compatible communication bus. For example, sensor 56 located adjacent to the UV emitter 30a can monitor the temperature and/or UV level within transparent housing 32a: information from sensor 56 can be processed by driver 40 to optimally operate UV emitter 30a, and in combination with the fluid UVT determined from sensors 46a and 46b be processed by driver 40 to determine degree of fouling of UV transparent housing 32a. Sensor 58 monitors the immediate ambient environment of driver 40. In all cases, the processing of such information allows the intelligent driver to respond appropriately.

Note that the number and type of parameters monitored by a single sensor 46 are not limited to those previously described: for example, a single sensor 46 can include means to sense fluid temperature and/or multiple UV sensing means to detect the UV level at a different locations within the treatment zone, without the need for multiple sensors. The fluid temperature sensor 46 signal can be alternatively used to provide an indication of the fluid flow condition: for example, if the UV emitter is ON the fluid temperature will rise in the case of a no-flow condition.

Figure 3:
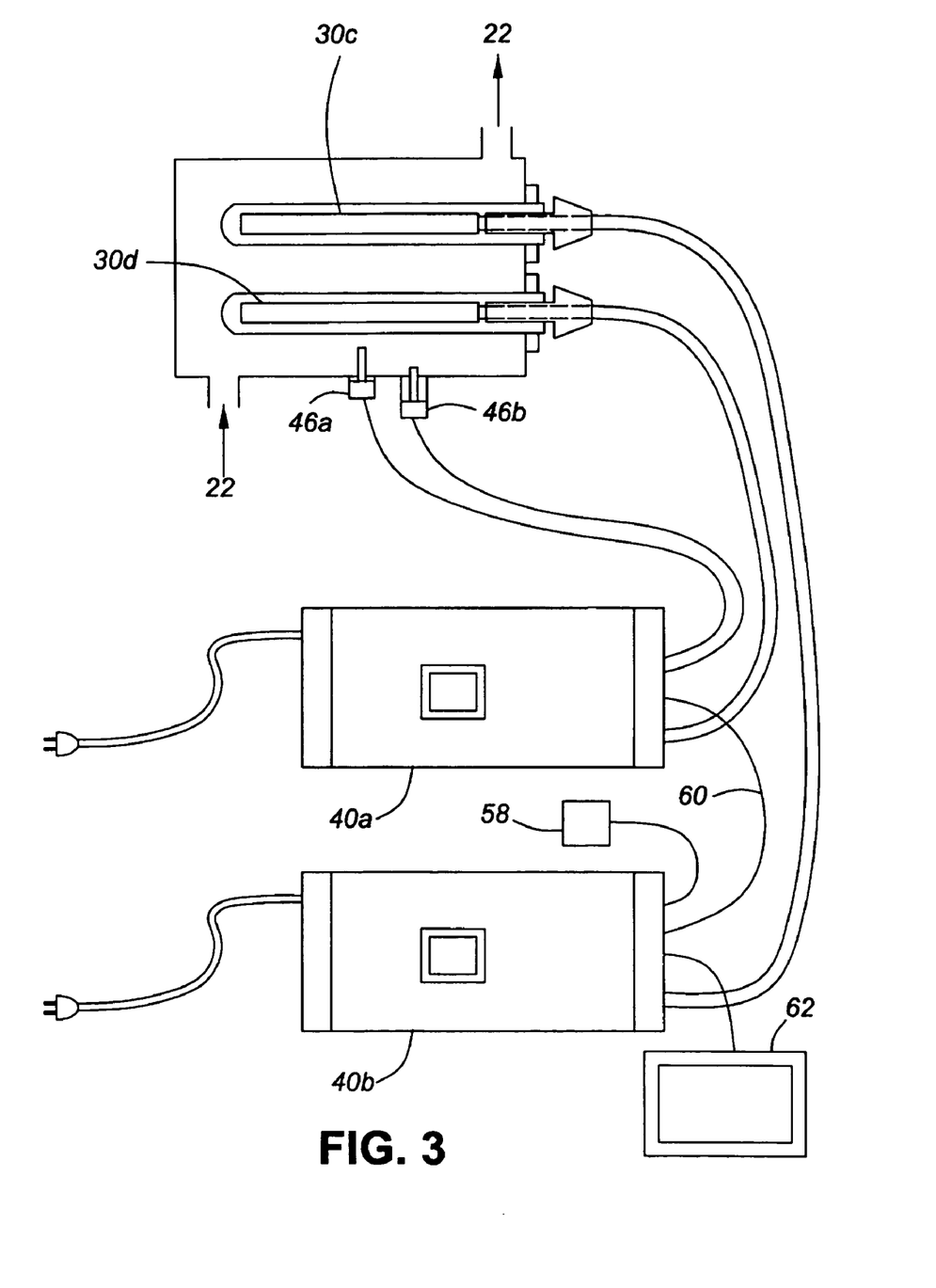
FIG. 3 is a fluid treatment system according to a further embodiment of the present invention.

FIG. 3 illustrates yet another system example embodiment in which multiple drivers 40a and 40b are connected respectively to multiple UV emitters 30c and 30d, and to each other via communication cable 60. Also note that sensors 46a, 46b, and 58 are also connected, and in this manner the sensor 46 information can be shared by both drivers 40a and 40b. Additional external devices, such as a remote display 62 can be connected to the system provided that they use a compatible communication bus.

Figure 4:
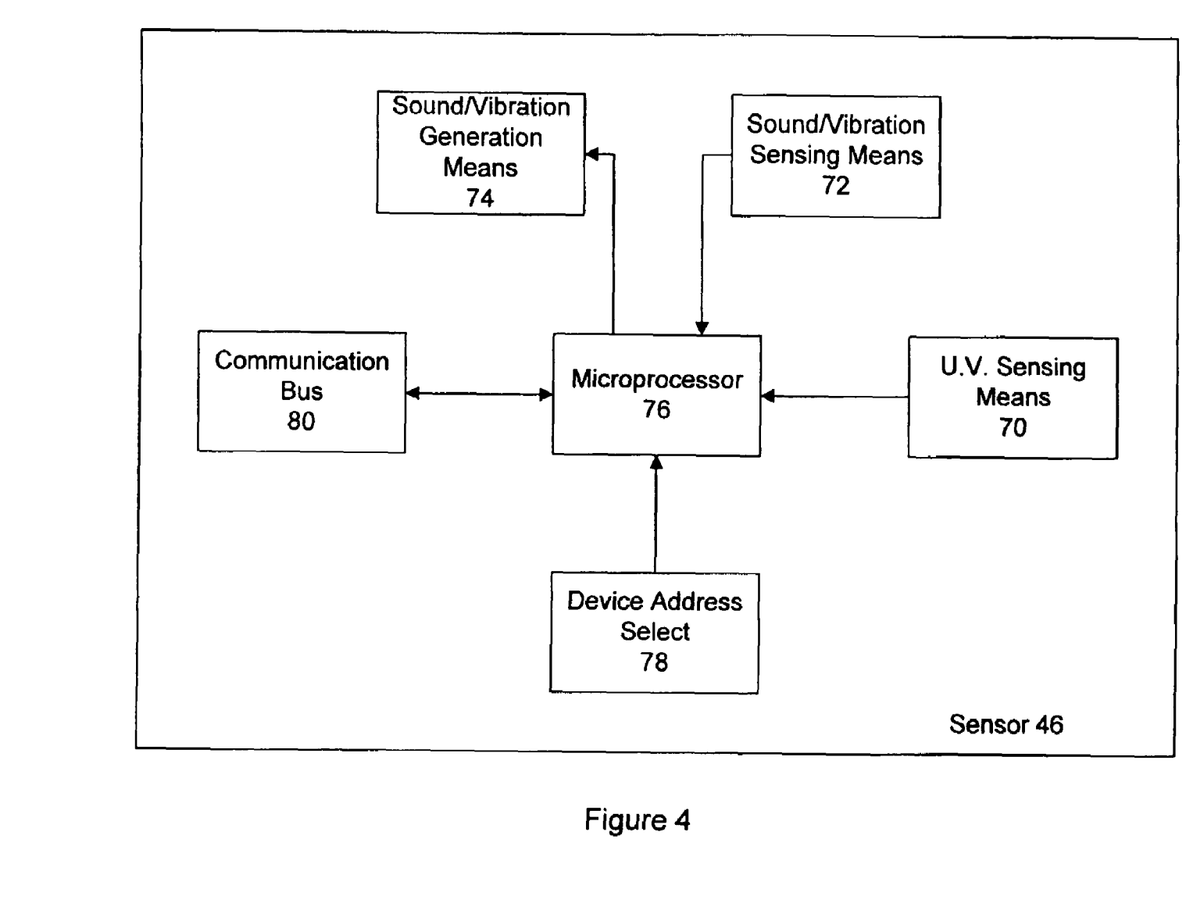
FIG. 4 is a block diagram of the hardware of the sensor of FIG. 1.

FIG. 4 is a block diagram of an example hardware arrangement contained within sensor 46. The following description pertains to the elements shown in FIG. 4: UV sensing means 70; sound/vibration sensing means 72; sound/vibration generation means 74; a microprocessor 76; a device address select means 78; and a communication bus 80.

The UV sensing means 70 is used to measure the intensity of the UV radiation. A possible embodiment for the UV sensing means 70 is a Silicon Carbon Photodiode and its associated signal amplification and processing electronics. Another possible embodiment for the UV sensing means 70 could utilize a photodiode sensitive to UV light but which is composed of materials other than silicon carbon: such photodiodes are readily available, but often require some attenuation or filtering of the UV light in order to prevent premature degradation of the diode. Another possible embodiment for the UV sensing means 70 is a regular photodiode and its associated signal amplification and processing electronics, suitable for measuring the visible light radiation produced by UV light incident on a fluorescent material. In all cases, a signal proportional to the incident UV light is produced by the UV sensing means 70.

A sound/vibration transducer is used as a means 72 for sensing the level of sound or vibration in the vessel to which it is attached. A possible embodiment of the sound/vibration sensing means 72 is a microphone and its associated signal amplification and processing electronics. Another possible embodiment of the sound/vibration sensing means 72 is a piezo-element and its associated signal amplification and processing electronics. In all cases, a signal proportional to sound/vibration is generated by the sound/vibration sensing means 72.

A sound/vibration generator is used to produce periodic sound and vibration signals. A possible embodiment of the sound/vibration generation means 74 is an acoustical sounder (or buzzer) and its associated drive electronics. Another possible embodiment of the sound/vibration generation means 74 is a piezo-element and its associated drive electronics. The sound/vibration generation means 74 is enabled and driven by the microprocessor 76 and is aligned so that the sounds/vibrations it generates can be detected by the sound/vibration generation means 74.

The microprocessor 76 is used to read, process and store the signal from the UV sensing means 70. The microprocessor 76 is also used to read, process and store the signal level of the sound/vibration sensing means 72, as well as to enable and drive the sound/vibration generation means 74. The microprocessor 76 is interfaced to a bi-directional communications bus 80 through which it both receives external command instructions and transmits data. A device address is used in each of the command instructions so that only the remote sensor 46 with the correct device address responds to the given command. The microprocessor 76 determines the appropriate device address by reading the device address select means 78. A possible embodiment of the microprocessor 76 for the UV sensor 46 is an 8-bit microcontroller.

The device address select means 78 is used to set the address of the sensor 46. A possible embodiment of the device address select means 78 is an array of switches interfaced to logic level input pins of the microprocessor 76. Another possible embodiment of the device address select means 78 is an array of switches and resistive divider network interfaced to an analog input of the microprocessor 76. Another possible embodiment of the device address select means 78 is a hardwired configuration of resistors interfaced to either the analog input or the logic level input pins of the microprocessor 76. Another possible embodiment of the device address select means 78 is a pre-programmed non-volatile memory value, located either internal to the microprocessor 76 via on-board EEPROM, or external to the microprocessor 76 via an EEPROM chip.

The communication bus is used to transfer command instructions to, and data from, the microprocessor 76. A possible embodiment of the communications bus 80 is a 2 wire I²C bus serial interface. Other possible embodiments of the communications bus 80 can include a high speed Serial Peripheral Interface (SPI), an RS-232 interface, an RS-485 interface, a USB interface, an IEEE 1394 interface, or a wireless RF interface.

Having reference to FIGS. 1 to 3, FIG. 5 is a flow chart of an example sensor operation code. A description of the operation code executed by the microprocessor contained within the sensor housing is as follows.

Figure 5:
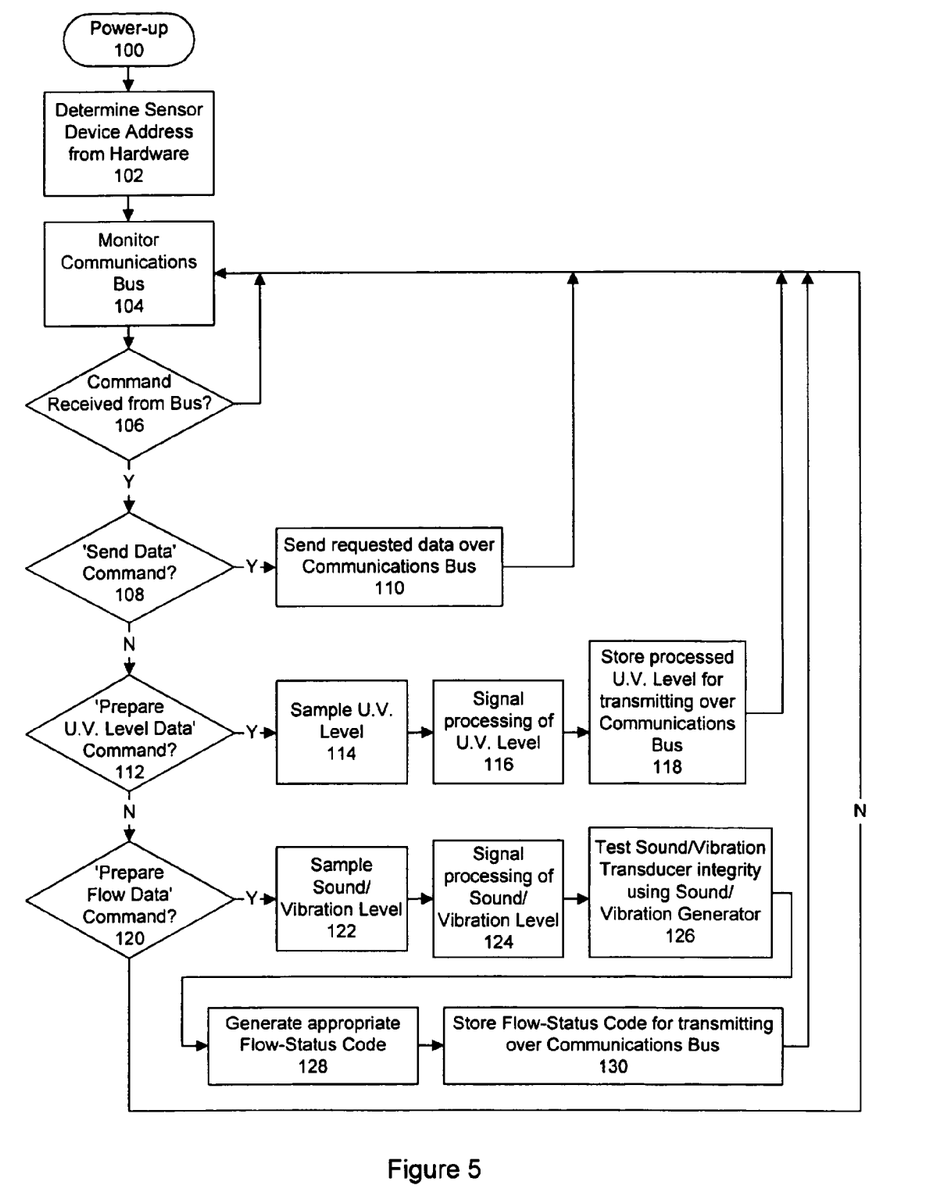
FIG. 5 is a flow chart of the sensor operation code of the present invention.

On Power-up (100) the microprocessor in the sensor 46 determines its unique device address (102) and begins to monitor (104) the communications bus 80 for valid communications to that device address. The remote sensor 46 periodically monitors the bus for any of four commands, namely the Send Data Command, the Prepare UV Level Data Command, the Test Sound Command, and the Prepare Flow Status Data Command.

Upon receipt (106) of the Send Data Command (108), the sensor 46 transmits (110) the current value of the Processed UV Level or the Flow-Status Code onto the communications bus 80. Upon receipt (112) of the Prepare UV Level Data Command, the sensor 46 samples (114), processes (116) and stores (118) the signal output of the UV Sensing Means. Upon receipt (120) of the Prepare Flow Status Data Command, the sensor 46 samples (122) and processes (124) the signal output from the sound/vibration sensing means 72. The remote sensor 46 then tests (126) the integrity of the measured Sound/Vibration Level by generating its own sound/vibration level to verify that there is a valid change in the output of the sound/vibration sensing means 72. If a valid change is not detected, then a sensor 46 failure signal can be generated. If a valid change is detected, then the appropriate Flow-Status Code is determined (128) by comparing the initially measured signal output from the sound/vibration sensing means 72 to a Flow Set Threshold Level. If the signal output is higher than or equal to the Flow Set Threshold Level, then the Flow Status Code is set to 1 (Flow is active) and stored. If the signal output is lower than the Flow Set Threshold Level, then the Flow-Status Code is set to 0 (Flow is inactive) and stored. The determined Code is then stored (130) for transmission over the communications bus.

Figure 6:
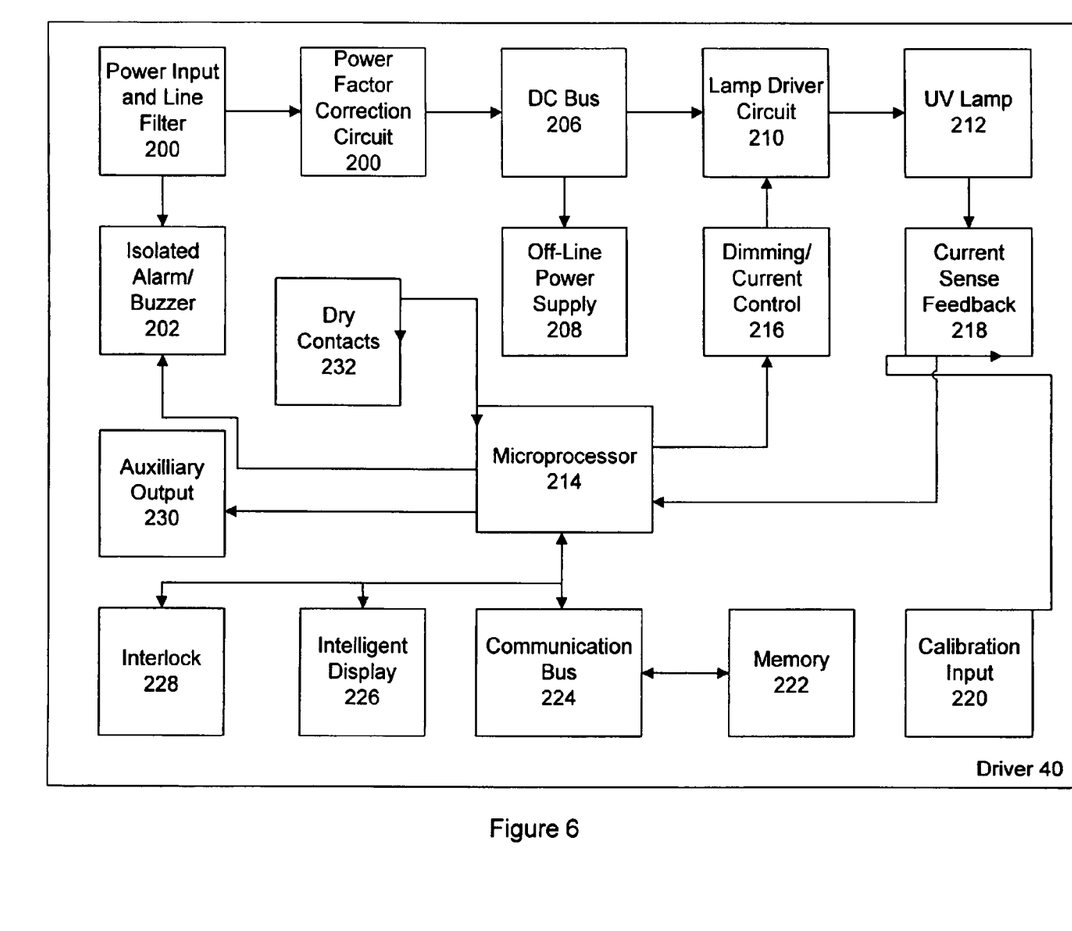
FIG. 6 is a block diagram of the hardware contained within the intelligent ballast/driver of FIG. 1.

FIG. 6 is a block diagram of example hardware contained within the intelligent driver, or ballast, 40. The following description pertains to the elements shown in FIG. 6 with reference to FIGS. 1 to 3.

The driver 40 contains a power input and line filter 200. The driver 40 can be operated from a 50/60 Hz line with a voltage ranging from 90 to 265 V AC. A fuse is used to limit the input current in the case of a fault condition in the driver 40. A transient voltage suppressor and an inrush current limiter are used to protect the ballast electronics from line voltage spikes and starting surge currents. A line filter is incorporated into the front end of the driver 40 in order to reduce the conducted EMI.

An isolated alarm/buzzer 202 is user to provide an audible alarm signal in case of ballast failure or during Low UV and other diagnostic conditions. The power to the timer IC is derived from an isolated power supply that remains active if the ballast fuse opens. The isolated alarm/buzzer 202 consists of a free-running timer IC connected directly to a piezoelectric speaker. An audible signal would be produced continuously were it not for the reset pin of the timer IC being pulled low via an opto-isolator output being controlled by an I/O port pin from the microprocessor. Hence, the microprocessor can turn on and off the isolated alarm in order to create unique alarm signals. If a catastrophic ballast failure were to occur, causing the microprocessor to fail, the opto-isolator could no longer be powered and the reset line of the timer IC could no longer be pulled low, thereby enabling a continuous alarm.

The driver 40 uses a power factor correction circuit 204 in order to provide near unity power factor operation over the entire line input voltage operation. The power factor correction circuit 204 consists of a bridge rectifier feeding a boost inductor. The boost inductor output is switched via a MOSFET and the current through the inductor is controlled using a transition mode, fixed on time, variable frequency switching pattern. A power factor control IC (MC34262 or ST L6561) is used to generate the switching pattern and control the output of the boost inductor into the DC bus 206.

The DC bus 206 is regulated at a nominal 400 V DC by the power factor control IC. The DC bus 206 is unaffected by fluctuations in the ballast input line voltage and provides a constant source of power for both the off-line power supply 208 and the lamp driver circuit 210.

The off-line power supply 208 consists of a high frequency switching DC to DC converter. This converter utilizes a Tiny Switch-II TNY264P IC from Power Integrations Inc. to derive an isolated +5 V DC, 3W power supply from the 400V DC bus 208. The +5 V DC is used to supply the microprocessor 214, memory 222, dry contacts 232, auxiliary outputs 230, dimming current control 216, intelligent display 226 and the communications bus 224.

The lamp driver circuit 210 consists of a fully integrated ballast control IC (IR21571) that is used to control the switching of two MOSFETS in a half bridge topology. The half bridge topology is used to feed a series resonant circuit comprised of an inductor and the parallel combination of a capacitor and the UV lamp. The ballast control IC is configured to switch power to the UV lamp from the DC bus 206 in a single lamp current mode heating configuration. The ballast control IC operates the UV lamp under either a Start, Pre-heat, Ignition or Run mode. The frequency and duration of the modes of operation are set by a series of resistor/capacitor combinations to the pins of the ballast control IC. A digital potentiometer, controlled from the microprocessor 214 via an opto-isolator interface, is used to adjust the value of the resistor that is used to set the Run mode frequency of the UV lamp 212. As the Run mode frequency of the lamp changes, so does the impedance of the series resonant circuit. Hence, the operating current of the lamp can easily be adjusted by the microprocessor 214 in order to follow a pre-set current control algorithm, or to simply adjust the lamp current to a desired level. The ballast control IC monitors the DC bus 206 for under-voltage. It also monitors the lamp current for the failure to strike and broken lamp filament conditions of near resonance and over-current operation. An opto-isolator is used to interface the shut-down pin of the ballast control IC to the microprocessor 214. Hence, the lamp driver circuit 210, and subsequent lamp operation, can be enabled or disabled through the microprocessor 214.

The UV lamp 212 consists of either Instant start, Pre-heat start, High output, or Amalgam type UV lamps. The UV lamp 212 is connected to the driver 40 using a 7 pin header. Although the lamps specifically listed are based of the mercury vapour type, other UV emitting technologies could be powered by the driver with appropriate reconfiguring of the lamp driver circuit.

The main microprocessor 214 consists of a PIC16F876-20/SO 8-bit CMOS FLASH microcontroller that is clocked at 20 MHz. It contains 8 KB of memory and has 5 channels of 10-Bit A/D and a Synchronous Serial Port (SSP). The microcontroller FLASH memory is programmed with a boot-loader section that can read data over the SSP and re-write its memory contents. Algorithms and data for the current control and the Intelligent Display operation can thereby be reprogrammed through the SSP via the communication bus 224. The individual screens for the intelligent display 56 are also programmed in the FLASH memory of the microcontroller. Additional screens can be read into the microcontroller via the communications bus from external memory on the driver 40. The microprocessor 214 enables/disables the operation of the lamp driver circuit 210 and also controls the operation of the ballast peripherals such as the dry contacts 232, auxiliary output 230, intelligent display 226, and the communication bus 224. The microprocessor utilizes its A/D converter to sense a voltage from the current sense feedback circuit and to check the integrity of the activation coil of the dry contacts 232.

A MAX5466 digital potentiometer is utilized to provide a dimming/current control 216 for the driver 40. The digital potentiometer is interfaced to the microprocessor 214 via an isolated two wire interface. The microprocessor 214 controls the wiper position of the digital potentiometer with a minimum 32-step resolution, thereby varying the total external resistance connected to the RT pin of the ballast control IC. A change in the external resistance at the RT pin will change the run frequency set-point of the balast control IC. As the run frequency is increased, the impedance of the series resonant circuit is increased as well, causing a proportional decrease in the true lamp current to the UV lamp 212.

A dual primary current sense transformer, Pulse part number PE-68383, is utilized to measure the true lamp current through the UV lamp 212. The primary windings are electrically connected in such a manner with the UV lamp filaments so that the magnetic fields produced by the filament currents are cancelled and only the magnetic field from the actual current through the UV lamp 212 is coupled to the secondary winding. The voltage produced at the secondary winding is rectified, filtered, and applied to the A/D input of the microprocessor 214. The leads from one of the primary windings of the current transformer are brought out to the calibration header for interface to the calibration input, thereby allowing a known reference current to be applied to the current sense feedback circuit 218 during calibration.

The calibration input 220 consists of a 6-pin header that is used to interface a known reference current to one of the windings of the ballast's current sense transformer. One of the pins of the header is connected to an input pin of the microprocessor 214. This input pin is pulled LO when the calibration header is connected, thereby indicating to the microprocessor 214 that calibration mode is to be initiated.

External EEPROM memory 222 is included on the driver 40 in order to store extra display screens and other data such as a load profile, alarm status history, and a flow/no-flow histogram. The memory 222 is interfaced to the microprocessor 214 using the communications bus 224 and an $I^2C$ communications protocol.

The communications bus 224 consists of a Serial Clock, Serial Data, +5 V Power and Common Return lines. The communications bus 224 is able to power and communicate with any compatible device that is connected to it that utilizes the $I^2C$ communications protocol. Peripherals such as EEPROM Memory, Screen Display Programmers, UV Sensors, and Wireless Alarm Transceivers can all be connected to the communications bus 224. A total of 128 separately identifiable devices can be connected to this communications bus 224.

The intelligent display 226 consists of a pushbutton switch integrated with a backlit programmable 36×24 pixel graphic LCD. An NKK Switches IS15ANCP4CF "Smart Switch" is utilized as the intelligent display 226 for the driver 40. The display 56 is backlit using red and green LEDs and can visually alert the user with three different backlit colours, namely red, green and amber. The display screens are written to the LCD via the microprocessor 214 and are refreshed at over 52 times per second. A printed circuit board header is used to extend the electrical connections to the intelligent display 226 so that the display 56 can be mounted to the case of the driver 40 where it can be viewed and touched. The pushbutton is activated by pressing the intelligent display. Pushbutton outputs are routed to the microprocessor 214 which monitors the pushbutton status and adjusts its algorithm execution depending on whether or not the display 56 was pressed.

An interlock 228 is created by routing the microprocessor reset pin and common lines to the 7-pin header used to connect the driver 40 to the UV lamp 212. These signal lines are connected to a normally closed pushbutton that is integrated into the UV lamp connector at the end that is connected to the UV cell. The pushbutton will be forced open if the UV lamp 212 is properly inserted and secured into the UV cell with the UV lamp connector. The pushbutton will close, disabling the microprocessor and shutting off the lamp driver circuit, as soon as the UV lamp connector is removed from the UV cell.

A microprocessor activated 5 V, 50 mA auxiliary output 230 is incorporated in the ballast circuit. This auxiliary output 230 can be used to activate a relay, flash an LED, interface to a Programmable Logic Controller, or trigger some other device.

Two sets of microprocessor-activated dry contacts 232 are incorporated in the ballast circuit. The contacts 232 can be configured as either normally open or normally closed and can be used to activate a solenoid valve, cleaning mechanism, or emergency shut-down relay. The relay contacts are rated for 15 A and 250 V AC to allow for a wide range of application.

In operation, once started, the microprocessor 214 causes the "Starting Self Test" and "Power Up" screens to be displayed for 2 seconds each. The microprocessor 214 then checks for communication with each active sensor 46 and displays pass or fail. If a sensor 46 fails, the microprocessor keeps checking for that sensor 46 in an endless loop until communication is established or the driver 40 is reset. Once all sensors have been checked, the microprocessor 214 continues on with the dry contact actuator check. The energizing coil for each dry contact is activated and tested for continuity. If a dry contact coil has failed, the microprocessor 214 keeps checking that dry contact in an endless loop until the coil is detected as being energized or the driver 40 is reset.

The search for the remote alarm is initiated once the dry contact check has been completed. The remote alarm address is broadcast on the I²C Bus and if no response is detected after a fixed period, the microprocessor 214 initiates the lamp starting procedure. If the microprocessor 214 detects a remote alarm, a test communication package is sent before proceeding to the lamp starting procedure.

In the Lamp Start/Restart mode, the microprocessor 214 enables the lamp driver 210 and waits 10 seconds for the ballast hardware to start the lamp. The true lamp current is sensed once 10 seconds have elapsed and if a minimum lamp current threshold is met, the lamp 212 is assumed to be fired and operating. Pass screens are displayed and the ballast control is executed according to Normal Mode.

If the sensed true lamp current is below the minimum lamp current threshold, the lamp 212 is assumed to have not fired and the lamp driver 210 is disabled. The flashing lamp failure alarm is activated and the lamp driver 210 is re-enabled after a one second wait. This one second wait ensures that the lamp driver 210 has been reset and that the lamp start sequence timing capacitors have had a chance to discharge. The microprocessor 214 will try to start the lamp 3 times. If after 3 attempts the lamp 212 has still not fired, the microprocessor 214 will leave the lamp driver 210 disabled and execute an endless loop by causing display of the lamp failure alarm.

Once the lamp has started, normal operation proceeds by displaying the Main Logo which typically consists of a customizable graphic that is designed to suit the end user. The Main Logo is illuminated by either Green, Amber, or Red depending on how many times that lamp life alarm has been deferred. The microprocessor 214 remains in this state, continuously calculating the cumulative lamp life, total ballast hours of operation, UV Level and flow. If the remote sensor 46 reports that there is no flow, the microprocessor 214 dims the lamp to a preset No-Flow intensity. Otherwise, if flow is detected, the microprocessor 214 ramps up the lamp intensity to full brightness.

When the microprocessor 214 detects a pushbutton press, the remaining lamp life is displayed for 10 seconds before returning to the Main Logo. The backlight for the remaining lamp life display is set to Green for a lamp life greater than 30 days, and Amber for a lamp life of 30 days or less. The display switches to Red once the lamp life has expired.

If a second pushbutton press is executed before 10 seconds have expired on the lamp life display, the microprocessor 214 switches the display 56 to the UV Level if flow has been detected, or to the Flow Status Screen if no flow has been detected. The Flow Status Screens alternate for 2 seconds each until 10 seconds expire, after which the microprocessor 214 causes re-display of the Main Logo. If the Pushbutton is pressed before 10 seconds expire on the Flow Status Screen, the microprocessor 214 switches the display to the Hours of Operation Screen.

The UV level screens are used to display the currently measured level of UV that is being reported from the UV sensor 46 to the user. The UV level is displayed with a green backlight if it is higher than 65% of its maximum rated value. An amber backlight is used if the displayed UV value is between 56% and 65% of its maximum rated value. The display 56 begins to flash red when the UV level drops below 56% and says red when the UV level drops below 50% of its maximum rated value. In cases where the display 56 was reporting other information (such as the Main Logo, the Total Hours of Operation, or the Remaining Lamp Life) the microprocessor 214 immediately switches to the UV level screens if Flow is detected and the UV level drops below 56% of its maximum rated value. A chirping alarm is activated via a buzzer to warn the user any time that UV level drops below 56%. The microprocessor 214 opens the dry contacts 232 and activates the buzzer 202 in a Low UV Level Alarm mode whenever the UV level falls below 50% of its maximum value. The UV level must then exceed 55% in order for the Low UV Level Alarm mode to be deactivated and the dry contacts 232 to be closed. A Low UV Level screen is displayed whenever the UV level drops below 30% of its maximum rated value.

If there is no Low UV alarm, the microprocessor 214 causes re-display of the Main Logo screen after 20 seconds of displaying the UV level screens. If the pushbutton is pressed before 20 seconds on the UV level screens expires, the microprocessor 214 causes display of the Total Hours of Operation screen. The cumulative total hours of ballast operation is displayed until either the pushbutton in pressed again, or 10 seconds has expired. In both cases, the microprocessor 214 will continue with displaying the Main Logo.

In calibration mode, a calibration mode jumper must be inserted onto the calibration header before power-up. On power-up, the ballast microprocessor 214 checks to see if the calibration jumper is present. If a calibration jumper is detected, the microprocessor 214 will immediately write the total cumulative hours of operation to the display 56. The microprocessor 214 then checks to see if the pushbutton was pressed. If a pushbutton press is detected, the microprocessor 214 sets the total cumulative hours of operation to zero, and waits for the pushbutton to be released. Once the pushbutton is released, the microprocessor 214 waits for 4 seconds and then enters the calibration mode. If a pushbutton was originally not detected, the microprocessor 214 waits for 5 seconds and enters the calibration mode.

The goal of the calibration procedure is to have the microprocessor 214 sense a simulated lamp current that is passed through the calibration header. This lamp current is to be used as the 100%, full power level that the driver 40 is to run the lamps at. Errors through current feedback and sense component tolerances are negated using this approach since the 100% lamp current is effectively translated into an 8-bit control set-point for the microprocessor. The microprocessor 214 senses the true lamp current and displays the measured value. If the measured value is in an allowed range of the full scale 0 to 255 measurement window (say somewhere between 128 and 200), the backlight of the display 56 is set to green. Otherwise, the backlight of the display 56 is set to red to indicate to the calibrator that the calibration current is either too high or too low to attain the proper resolution required for controlling the lamp current. If the calibrator presses the pushbutton when the display backlight is green, the currently displayed value of the sensed true lamp current is set by the microprocessor as the 100% current level in the dimming control algorithm, and is written to its FLASH memory. The microprocessor 214 derives the No Flow dimming set-point from this value using a preset scaling factor, say 60%. The 100% current level set operation is disabled whenever the display backlight is red, thereby preventing the calibrator from setting an inappropriate value for the 100% current level setpoint.

The above-described embodiments of the present invention are intended to be examples only. Alterations, modifications and variations can be effected to the particular embodiments by those of skill in the art without departing from the scope of the invention, which is defined solely by the claims appended hereto.

What is claimed is:

1. An ultraviolet (UV) fluid treatment system for small enterprise and consumer use, comprising:
    a fluid treatment zone having a fluid inlet and a fluid outlet
    a UV emitter mounted within the fluid treatment zone;
    a sensor unit disposed within the fluid treatment zone, the sensor unit including at least fluid flow sensing means to sense fluid flow within the fluid treatment zone and UV sensing means to sense UV light levels;
    an intelligent driver for receiving a fluid flow indication and a UV light level indication from the sensor unit, and for controlling operation of the UV emitter in response to at least one of the fluid flow indication and the UV light level indication; and
    an indicator in communication with the intelligent driver for providing a user with information related to operation of the fluid treatment system.

2. The UV fluid treatment system of claim 1, wherein the UV emitter is a mercury vapour lamp.

3. The UV fluid treatment system of claim 1, wherein the sensor unit is self-contained within a housing.

4. The UV fluid treatment system of claim 1, wherein the sensor unit is remote from the UV emitter.

5. The UV fluid treatment system of claim 1, wherein the fluid flow sensing means includes sound/vibration sensing means.

6. The UV fluid treatment system of claim 5, wherein the fluid flow sensing means includes sound/vibration generation means.

7. The UV fluid treatment system of claim 5, wherein the sensor unit includes a sensor microprocessor for reading a signal level from the sound/vibration sensor, for processing the signal level to determine the fluid flow indication, and for providing the fluid flow indication to the intelligent driver.

8. The UV fluid treatment system of claim 1, further including auxiliary sound generation means disposed within the fluid treatment zone.

9. The UV fluid treatment system of claim 8, wherein the auxiliary sound generation means is a sound generating paddlewheel disposed in a fluid flow path between the fluid inlet and the fluid outlet.

10. The UV fluid treatment system of claim 8, wherein the auxiliary sound generation means is a sound generation reed disposed at the fluid inlet.

11. The UV fluid treatment system of claim 1, wherein the intelligent driver includes a lamp driver circuit under control of a ballast microprocessor.

12. The UV fluid treatment system of claim 11, wherein the ballast microprocessor is reprogrammable.

13. A sensor unit for an ultraviolet (UV) fluid treatment system for small enterprise and consumer use, comprising:
    a plurality of sensing means contained within a housing, the housing permitting the plurality of sensing means to be mounted within a fluid treatment zone of the UV fluid treatment system; and
    a sensor microprocessor, contained within the housing, for reading and processing information received from the plurality of sensing means to provide operational parameters to an intelligent driver controlling a UV emitter disposed within the fluid treatment zone.

14. The sensor unit of claim 13, wherein the plurality of sensing means includes fluid flow sensing means to sense fluid flow within the fluid treatment zone, and UV sensing means to sense UV light levels within the fluid treatment zone.

15. The sensor unit of claim 14, wherein the fluid flow sensing means includes sound/vibration sensing means.

16. The sensor unit of claim 15, wherein the fluid flow sensing means includes sound/vibration generation means.

17. The sensor unit of claim 15, wherein the sound/vibration sensing means is a microphone.

18. The sensor unit of claim 15, wherein the sound/vibration generation means is an acoustical sounder.

19. The sensor unit of claim 15, wherein the sound/vibration generation means is a piezo-element.

20. The sensor unit of claim 13, wherein the sensor microprocessor receives information relating to fluid from auxiliary sound generation means.

21. An intelligent driver for an ultraviolet (UV) emitter disposed within a fluid treatment zone in a fluid treatment system for small enterprise and consumer use, comprising:
    a ballast microprocessor for receiving a plurality of fluid condition indications from a sensor unit disposed within the fluid treatment zone, and for controlling operation of the UV emitter in response to at least one of the fluid condition indications; and
    an indicator in communication with the ballast microprocessor for providing a user with information related to operation of the fluid treatment system.

22. The intelligent driver of claim 21, wherein the plurality of fluid condition indications includes a fluid flow indication and a UV light level indication.

23. The intelligent driver of claim 21, including a lamp driver circuit under control of the ballast microprocessor.

24. The intelligent driver of claim 21, including an alarm for indicating system malfunction to a user.

25. The intelligent driver of claim 21, including a safety interlock for detecting improper connection of the UV emitter.

26. The intelligent driver of claim 21, wherein the ballast microprocessor is re-programmable.

27. The intelligent driver of claim 21, wherein the indicator includes a display for displaying at least one of text and graphics.

\* \* \* \* \*